(12) United States Patent
Taniguchi et al.

(10) Patent No.: US 10,399,915 B2
(45) Date of Patent: Sep. 3, 2019

(54) MANUFACTURING METHOD OF 1-CHLORO-2,3,3,3-TETRAFLUOROPROPENE

(71) Applicant: AGC Inc., Chiyoda-ku (JP)

(72) Inventors: Tomoaki Taniguchi, Chiyoda-ku (JP); Shoji Furuta, Chiyoda-ku (JP); Hidefumi Shiota, Chiyoda-ku (JP)

(73) Assignee: AGC Inc., Chiyoda-ku (JP)

( * ) Notice: Subject to any disclaimer, the term of this patent is extended or adjusted under 35 U.S.C. 154(b) by 0 days.

(21) Appl. No.: 15/929,024

(22) Filed: Jun. 20, 2018

(65) Prior Publication Data

US 2018/0297918 A1  Oct. 18, 2018

Related U.S. Application Data

(63) Continuation of application No. PCT/JP2016/088052, filed on Dec. 21, 2016.

(30) Foreign Application Priority Data

Dec. 25, 2015  (JP) .................................. 2015-254136

(51) Int. Cl.
*C07B 61/00* (2006.01)
*C07C 17/04* (2006.01)
(Continued)

(52) U.S. Cl.
CPC .............. *C07C 17/25* (2013.01); *C07C 17/04* (2013.01); *C07C 19/10* (2013.01); *C07C 21/18* (2013.01); *C07B 61/00* (2013.01)

(58) Field of Classification Search
CPC .......... C07C 17/04; C07C 17/25; C07C 19/14; C07C 21/18
See application file for complete search history.

(56) References Cited

U.S. PATENT DOCUMENTS

| 4,324,930 A | 4/1982 | Von Halasz |
| 5,705,716 A * | 1/1998 | Li .......................... C07C 19/10 |
| | | 570/134 |

(Continued)

FOREIGN PATENT DOCUMENTS

| CA | 1 158 678 | 12/1983 |
| CN | 1589248 | 3/2005 |

(Continued)

OTHER PUBLICATIONS

International Search Report dated Apr. 4, 2017 in PCT/JP2016/088052 filed Dec. 21, 2016 (with English Translation).

(Continued)

*Primary Examiner* — Jafar F Parsa
(74) *Attorney, Agent, or Firm* — Oblon, McClelland, Maier & Neustadt, L.L.P.

(57) ABSTRACT

There is provided an economically advantageous manufacturing method capable of efficiently obtaining 1-chloro-2,3,3,3-tetrafluoropropene by using 1,2-dichloro-2,3,3,3-tetrafluoropropane as a raw material. A manufacturing method of 1-chloro-2,3,3,3-tetrafluoropropene is characterized in that it includes subjecting 1,2-dichloro-2,3,3,3-tetrafluoropropane to a dehydrochlorination reaction in a liquid phase in a presence of a base.

12 Claims, 1 Drawing Sheet

(51) Int. Cl.
*C07C 17/25* (2006.01)
*C07C 19/10* (2006.01)
*C07C 21/18* (2006.01)

(56) References Cited

U.S. PATENT DOCUMENTS

| | | |
|---|---|---|
| 2003/0060670 A1 | 3/2003 | Nair et al. |
| 2008/0076950 A1* | 3/2008 | Rao .................. B01J 19/02 585/500 |
| 2011/0319678 A1 | 12/2011 | Seki et al. |
| 2012/0215037 A1 | 8/2012 | Sun et al. |
| 2015/0038749 A1 | 2/2015 | Imura et al. |

FOREIGN PATENT DOCUMENTS

| | | |
|---|---|---|
| CN | 103370292 | 10/2013 |
| DE | 30 12 005 A1 | 10/1981 |
| EP | 0 037 003 | 10/1981 |
| JP | 56-150027 | 11/1981 |
| JP | 2005-504097 | 2/2005 |
| JP | 2014-513673 | 6/2014 |
| JP | 2014-237627 | 12/2014 |
| JP | 5713016 | 5/2015 |
| JP | 2015-120670 | 7/2015 |
| KR | 1020040044993 | 5/2004 |
| KR | 10-2014-0008384 | 1/2014 |
| MX | 2013009580 | 9/2013 |
| TW | 201235333 A1 | 9/2012 |
| WO | 03/027051 A1 | 4/2003 |
| WO | WO 2012/115930 A1 | 8/2012 |

OTHER PUBLICATIONS

Written Opinion dated Apr. 4, 2017 in PCT/JP2016/088052 filed Dec. 21, 2016.

* cited by examiner

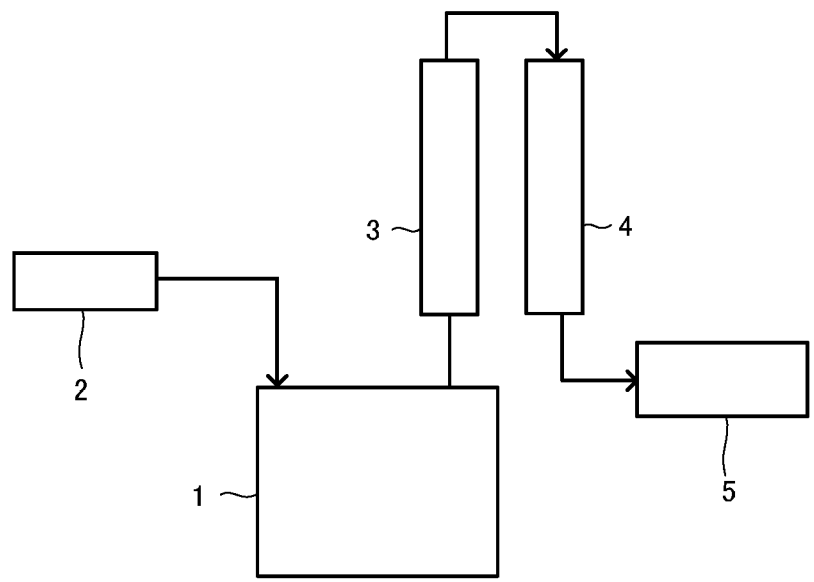

MANUFACTURING METHOD OF 1-CHLORO-2,3,3,3-TETRAFLUOROPROPENE

CROSS-REFERENCE TO RELATED APPLICATIONS

This application is a continuation of prior International Application No. PCT/JP2016/088052, filed on Dec. 21, 2016 which is based upon and claims the benefit of priority from Japanese Patent Application No. 2015-254136, filed on Dec. 25, 2015; the entire contents of all of which are incorporated herein by reference.

FIELD

The present invention relates to a method of manufacturing 1-chloro-2,3,3,3-tetrafluoropropene.

BACKGROUND

Recently, as a working fluid for a heat cycle system such as a refrigerant for a refrigerator, a refrigerant for an air-conditioning apparatus, a working fluid for a power generation system (such as an exhaust heat recovery power generation), a working fluid for a latent heat transport apparatus (such as a heat pipe), or a secondary cooling fluid, expectations are concentrated on hydrofluoroolefin (HFO), namely, hydrofluorocarbon (HFC) having a carbon-carbon double bond. HFO attracts attention as a working fluid having less effect on the ozone layer and less effect on global warming since the carbon-carbon double bond is likely to be decomposed by OH radicals in the air. Note that in the present specification, saturated HFC is referred to as HFC, and discriminated from HFO unless otherwise stated.

As a working fluid having not only less effect on the ozone layer and less effect on global warming but also low combustibility, there are hydrochlorofluoroolefin (HCFO) such as hydrochlorofluoropropene and chlorofluoroolefin (CFO) having a high ratio of halogen which reduces combustibility and having a carbon-carbon double bond which is likely to be decomposed by OH radicals in the air. Further, as hydrochlorofluoropropene, there is known 1-chloro-2,3,3,3-tetrafluoropropene (CClH=CF—CF$_3$, HCFO-1224yd).

In the present specification, regarding halogenated hydrocarbon, an abbreviated name of the compound is mentioned in parentheses behind a compound name, and the abbreviated name is used instead of the compound name according to need. Further, only numeric characters and lower-case characters of alphabet behind a hyphen (-) ("1224yd" in "HCFO-1224yd", for example) are sometimes used as the abbreviated name. Further, in 1224yd, a Z-isomer and an E-isomer which are geometric isomers exist according to positions of substituents bonded to carbon having a double bond. When the compound name or the abbreviated name of the compound is used unless otherwise stated regarding the compound with respect to which the Z-isomer and the E-isomer exist in the present specification, the Z-isomer, the E-isomer, or a mixture having an arbitrary ratio of the Z-isomer and the E-isomer is indicated. When (Z) or (E) is denoted behind the compound name or the abbreviated name of the compound, a Z-isomer or an E-isomer of each compound is indicated.

As a method of manufacturing 1224yd, Patent Reference 1 (JP-A No. 2014-513673) discloses a method in which 1,2-dichloro-2,3,3,3-tetrafluoropropane (CClH$_2$—CFCl—CF$_3$, HCFC-234bb) is subjected to a dehydrochlorination reaction at a temperature of 200 to 500° C. by using, as a catalyst, carbon (activated carbon) which is subjected to pretreatment such as acid cleaning, and on which alkali metal salt is supported.

However, in order to increase a conversion ratio of 234bb in the method described in Patent Reference 1, the pretreatment (acid cleaning) of carbon being the catalyst is required, and the performance of the catalyst changes greatly depending on the method of treatment, so that it takes a lot of time to adjust the catalyst including the pretreatment. Further, in the method of Patent Reference 1, an operating life of the catalyst is short, and a raw material conversion ratio is reduced greatly within 120 hours from the start of the reaction, so that it is difficult to cause a stable reaction for a long period of time, although reproduction of the catalyst is possible.

Further, the method of Patent Reference 1 uses a source gas in which an inert gas (N$_2$ gas) is mixed in 234bb, so that a cost for the inert gas is required, and in addition to that, it is necessary to separate the inert gas from a product, which requires a cost for equipment for recovery, and the like.

Besides, in the method of Patent Reference 1, the dehydrochlorination reaction is caused at a temperature of 200 to 500° C., and in order to increase the conversion ratio of 234bb and selectivity of 1224yd, it is required to cause the reaction at a temperature in the vicinity of 400° C. For this reason, an energy cost is required, which is a problem. As described above, it cannot be said that the method described in Patent Reference 1 is an economically advantageous manufacturing method.

SUMMARY

The present invention has been made to solve the above-described problems, and an object thereof is to provide an economically advantageous manufacturing method capable of efficiently obtaining 1-chloro-2,3,3,3-tetrafluoropropene (HCFO-1224yd) by using 1,2-dichloro-2,3,3,3-tetrafluoropropane (HCFC-234bb) as a raw material.

In the present specification, regarding halogenated hydrocarbon, an abbreviated name of the compound is mentioned in parentheses behind a compound name, and the abbreviated name is used instead of the compound name according to need. Further, only numeric characters and lower-case characters of alphabet behind a hyphen (-) ("1224yd" in "HCFO-1224yd", for example) are sometimes used as the abbreviated name. Further, in 1224yd, a Z-isomer and an E-isomer which are geometric isomers exist according to positions of substituents bonded to carbon having a double bond. When the compound name or the abbreviated name of the compound is used unless otherwise stated regarding the compound with respect to which the Z-isomer and the E-isomer exist in the present specification, the Z-isomer, the E-isomer, or a mixture having an arbitrary ratio of the Z-isomer and the E-isomer is indicated. When (Z) or (E) is denoted behind the compound name or the abbreviated name of the compound, a Z-isomer or an E-isomer of each compound is indicated.

The present invention provides a manufacturing method of 1224yd having the configuration of the following [1] to [12].

[1] A manufacturing method of 1224yd, the method including subjecting 234bb to a dehydrochlorination reaction in a liquid phase in a presence of a base.

[2] The manufacturing method according to [1], wherein 234bb is subjected to the dehydrochlorination reaction in the liquid phase in a presence of a solvent to dissolve the base, and the base.

[3] The manufacturing method according to [1], wherein the base is at least one kind of base selected from a group consisting of a metal hydroxide, a metal oxide, and a metal carbonate.

[4] The manufacturing method according to [1], wherein the base is used in a ratio of 0.2 to 2.5 mol with respect to 1 mol of the 234bb.

[5] The manufacturing method according to [1], wherein a reaction temperature in the dehydrochlorination reaction is 40 to 100° C.

[6] The manufacturing method according to [2], wherein the solvent is water.

[7] The manufacturing method according to [2], wherein an amount of the base is 10 to 50 mass % with respect to total mass of the solvent and the base.

[8] The manufacturing method according to [1], wherein the dehydrochlorination reaction is performed in a presence of a phase-transfer catalyst.

[9] The manufacturing method according to [8], wherein the phase-transfer catalyst is a quaternary ammonium salt.

[10] The manufacturing method according to [9], wherein the quaternary ammonium salt is at least one selected from a group consisting of tetra-n-butylammonium chloride, tetra-n-butylammonium bromide, and methyltri-n-octylammonium chloride.

[11] The manufacturing method according to [1], the method further including making 2,3,3,3-tetrafluoropropene (HCFO-1234yf) and chlorine react with each other to obtain 234bb.

[12] The manufacturing method according to [11], wherein a reaction of the 1234yf and chlorine is caused under irradiation of light in a wavelength region of 400 to 750 nm.

According to the present invention, it is possible to manufacture 1224yd with a high conversion ratio and high selectivity by using 234bb as a raw material. Further, according to the present invention, pretreatment of a catalyst is not required, and besides, an operating life of the catalyst is long, so that a dehydrochlorination reaction can be stably maintained with a small number of processes. Furthermore, an energy cost is low since the dehydrochlorination reaction can be caused at a relatively low temperature, and besides, it is not required to provide processes or equipment for separating and recovering an inert gas from a product since there is no need to use the inert gas for supplying the raw material, which is economically advantageous.

BRIEF DESCRIPTION OF THE DRAWINGS

FIG. 1 is a flow chart illustrating one example of an embodiment of the present invention.

MODES FOR CARRYING OUT THE INVENTION

A manufacturing method of 1224yd of the present invention is a method in which 234bb is subjected to a dehydrochlorination reaction in a liquid phase in the presence of a base. The dehydrochlorination reaction is preferably carried out, in the presence of a solvent to dissolve the base and the base, while making 234bb to be brought into contact with the base dissolved in the solvent, in a liquid phase. Further, it is preferable to cause the reaction in a state where a raw material and a product are uniformly distributed in a reaction system.

<Dehydrochlorination Reaction of 234bb>
The dehydrochlorination reaction of 234bb according to the manufacturing method of the present invention is represented by the following formula (1).

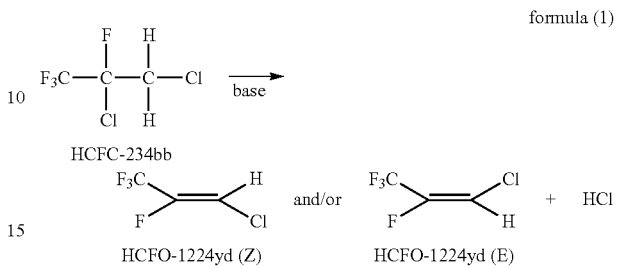

1224yd obtained through the manufacturing method of the present invention has a high ratio of halogen which reduces combustibility and besides, it has a carbon-carbon double bond which is likely to be decomposed by OH radicals in the air in a molecule, so that it has low combustibility, less effect on the ozone layer and less effect on global warming. Therefore, 1224yd has high availability as a working fluid for a heat cycle system.

1224yd obtained through the manufacturing method of the present invention may be only the Z-isomer, only the E-isomer, or the mixture of the Z-isomer and the E-isomer. 1224yd (Z) being the Z-isomer has chemical stability higher than that of 1224yd (E) being the E-isomer, and is more preferable as a working fluid for a heat cycle system. Further, according to the manufacturing method of the present invention, it is possible to efficiently manufacture 1224yd which necessarily contains 1224yd (Z). Furthermore, according to the manufacturing method of the present invention, it is possible to obtain 1224yd in which a content ratio of 1224yd (Z) is higher than a content ratio of 1224yd (E).

<Manufacture of 234bb>
234bb used for the manufacturing method of the present invention is a publicly-known compound known as a manufacturing raw material or an intermediate of a fluorine-containing compound, and can be manufactured through a publicly-known method. For example, 234bb can be manufactured by making 2,3,3,3-tetrafluoropropene (HFO-1234yf) and chlorine react with each other as represented by the following formula (2).

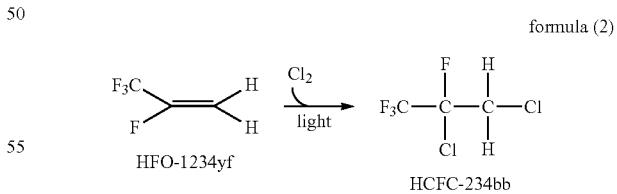

1234yf being a starting material in the reaction represented by the formula (2) (which is referred to as reaction (2), hereinafter) has quite low global warming potential, so that a demand for 1234yf as a working fluid for a heat cycle system is increasing in recent years. 1234yf can be manufactured through a publicly-known manufacturing method. As a manufacturing method of 1234yf, there can be cited a method described in the specification of U.S. Pat. No. 5,713,016, for example.

From a viewpoint of increasing a reaction rate, the reaction (2) is preferably carried out under irradiation of light. The light used for irradiation is preferably visible light because it is possible to suppress by-production of 1,1,2-trichloro-2,3,3,3-tetrafluoropropane (HCFC-224ba) and 1,1,1,2-tetrachloro-2,3,3,3-tetrafluoropropane (CFC-214bb) being perchlorinated bodies of 1234yf, and to increase selectivity of 234bb being an object product. The visible light is light whose short-wavelength limit is 360 to 400 nm and whose long-wavelength limit is 760 to 830 nm. A wavelength of the light used for the irradiation is preferably 400 to 750 nm, and more preferably 420 to 730 nm. Note that the light used for the irradiation may partially include light with a wavelength of less than 400 nm or light with a wavelength of greater than 750 nm.

When high-energy ray having a wavelength of less than 400 nm is used for the reaction (2) by using a high-pressure mercury lamp, a low-pressure mercury lamp, a metal halide lamp, or the like, for example, the reaction is likely to be excessively activated, and it is likely to be difficult to control the reaction. For this reason, it is preferable to use the light having the wavelength of 400 nm or more. The light used for the reaction (2) may be one excluding the light with the wavelength of less than 400 nm.

Note that a conversion ratio indicates a ratio (mol %) of an amount of the raw material consumed due to the reaction with respect to the total amount of the raw material used for the reaction, and selectivity indicates a ratio (mol %) of a generated amount of an object product with respect to the total amount of the product.

If the light used for the reaction (2) is light having a wavelength of 750 nm or less, the reaction is activated, and the reaction is likely to progress efficiently. The light with the wavelength of greater than 750 nm is difficult to exert influence on the selectivity of 234bb being the object product, so that the light used for the reaction may include the light with the wavelength of greater than 750 nm.

As a light source capable of efficiently irradiating light with a wavelength of 400 to 750 nm to the raw material in the reaction (2), there can be cited a fluorescent light, an incandescent light, an LED light, or the like, for example. The light with the wavelength of less than 400 nm included in light obtained by the fluorescent light or the incandescent light may also be excluded by using a filter or the like.

A method of irradiating the light to the raw material in the reaction (2) is not particularly limited as long as it is a method capable of uniformly irradiating the light to the entire reaction solution containing the raw material, a solvent, and a product throughout a reaction time. For example, there can be cited a method in which a light source wearing a jacket is inserted into the reaction solution, and the light is irradiated to the raw material in the reaction solution from the inside of the reaction solution, and the like. The jacket is preferably made of a material which transmits at least light with the wavelength useful for the aforementioned reaction, is inert to the components contained in the reaction solution, and is difficult to be corroded by these components. Further, in a case where the light source generates heat, the aforementioned jacket preferably has a cooling means depending on the reaction temperature.

In the reaction (2), each of 1234yf and chlorine may be separately supplied to a reactor or they may also be supplied in a previously mixed state. Further, 1234yf and chlorine may be respectively supplied in a gaseous state or in a liquid state.

A ratio between 1234yf and chlorine to be supplied is preferably 0.5 to 2.0, and more preferably 0.8 to 1.2 as a ratio between a supply molar quantity of chlorine and a supply molar quantity of 1234yf (which is also referred to as "chlorine/1234yf", hereinafter), from a viewpoint of activating the reaction and a viewpoint of suppressing by-products to increase the selectivity of 234bb.

The reaction (2) is normally carried out in a reactor in which a mixed solution obtained by dissolving the raw material in a solvent is put. A reaction temperature is preferably 0 to 100° C., and more preferably 5 to 60° C., from a viewpoint of increasing a reaction rate. A pressure in the reactor is preferably 0 to 1 MPa, and more preferably 0.05 to 0.5 MPa so that the manufacture can be realized efficiently. In order to improve the productivity, it is preferable to cause the reaction under a condition of added pressure. In the present specification, the pressure indicates a gauge pressure, unless otherwise noted.

A material of the reactor is not particularly limited as long as it is a material which is inert to components contained in a reaction solution, and difficult to be corroded by these components. As the material of the reactor, there can be cited, for example, iron, nickel, an alloy containing these as main components, glass, resin, and so on. From a viewpoint of pressure resistance and corrosion resistance, a reactor made of the aforementioned alloy and whose inner surface is lined with resin is preferable.

The reaction (2) may be performed in any of a semi-continuous mode, a batch mode, and a continuous mode. The reaction time can be appropriately adjusted by a general method depending on each of the modes. Regarding the supply of the raw material to the reactor, it is possible to employ a method in which each predetermined amount for each component of the raw material is supplied, or a method in which the raw material is supplied as a mixture containing each predetermined amount of each component. The supply of the raw material may be performed by diluting the raw material with inert gas such as nitrogen according to need.

In the semi-continuous mode, the raw material is added to be supplied at a certain rate during the reaction as each component of the raw material or as a mixture as a result of mixing each component of the raw material. The raw material may be added in an intermittent manner or continuous manner. In the batch mode, the raw material is prepared in the reactor together with the solvent and the like before the reaction, and then subjected to the reaction.

In the continuous mode, the raw material is continuously supplied, during the reaction, from a lower part of the reactor in which the solvent is prepared, for example. In the continuous mode, the product after the completion of the reaction is continuously taken out, through overflow or the like, for example, from an upper part of the reactor.

When the reaction (2) is caused, it is preferable to perform stirring by using ordinary method, device, and the like, in each of the semi-continuous mode, the batch mode, and the continuous mode.

The product obtained in a manner as described above contains 234bb being the object product, the unreacted raw material, the solvent, the by-product, and so on. As the by-product, there can be cited 1,1,2-trichloro-2,3,3,3-tetrafluoropropane (224ba), 1,1,1,2-tetrachloro-2,3,3,3-tetrafluoropropane (214bb), and so on.

As a method of separating 234bb being the object product from the obtained product, there can be cited, for example, an ordinary separation method such as a method in which chlorine is removed through cleaning with alkali, and then the solvent and the by-product are removed through distillation. Further, by performing the distillation, it is possible to refine 234bb, and by repeatedly performing the distillation, it is possible to obtain 234bb with desired purity.

<Manufacture of 1224yd>

The manufacturing method of 1224yd of the present invention is characterized in that 234bb is subjected to the dehydrochlorination reaction in accordance with the aforementioned reaction formula (1) in the liquid phase in the presence of the base. In the manufacturing method of the present invention, as 234bb being the starting material in the reaction represented by the formula (1) (referred to as reaction (1), hereinafter), it is possible to use 234bb obtained by the above-described method. Note that a method of obtaining 234bb is not limited to this.

Conceptually, the starting material in the reaction (1) preferably contains no impurities other than 234bb, and, it may contain impurities from an economic point of view. The impurity is preferably a compound which does not inhibit the dehydrochlorination reaction of 234bb. As the impurity, one being a chlorinated substance of 1234yf, except 234bb, can be cited, and 224ba, 214bb, and so on can be exemplified.

When the impurities are contained, a ratio of 234bb with respect a total amount of the impurities and 234bb is preferably 85 mass % or more and less than 100 mass %, and more preferably not less than 90 mass % nor more than 99 mass %.

The starting material in the reaction (1) is preferably one containing 234bb as a main component and containing at least one kind of compound selected from 224ba and 214bb. A ratio of the total amount of 224ba and 214bb being the impurities is preferably greater than 0 mol % and 15 mol % or less, and more preferably not less than 0.1 mol % nor more than 7 mol % with respect to the total amount of the impurities and 234bb, in order to efficiently manufacture 1224yd.

The base in the reaction (1) is not particularly limited as long as it is a base capable of carrying out the dehydrochlorination reaction of the reaction (1). The base is preferably at least one selected from a group consisting of a metal hydroxide, a metal oxide, and a metal carbonate.

As the metal hydroxide, there can be cited an alkaline-earth metal hydroxide, an alkali metal hydroxide, and so on. As the alkaline-earth metal hydroxide, magnesium hydroxide, calcium hydroxide, strontium hydroxide, or barium hydroxide is preferable, and as the alkali metal hydroxide, lithium hydroxide, sodium hydroxide, or potassium hydroxide is preferable. One kind of the base may be used or two kinds or more thereof may be used in combination.

As the metal oxide, there can be cited an alkali metal oxide, an alkaline-earth metal oxide, and so on. As the alkali metal oxide, sodium oxide is preferable, and as the alkaline-earth metal oxide, calcium oxide is preferable. Further, the metal oxide may be an oxide of one kind of metal or may be a composite oxide of two kinds or more of metals.

As the metal carbonate, there can be cited an alkaline-earth metal carbonate, an alkali metal carbonate, and so on. As the alkaline-earth metal carbonate, there can be cited a carbonate of beryllium, magnesium, calcium, strontium, barium, or radium. As the alkali metal carbonate, there can be cited a carbonate of lithium, sodium, potassium, rubidium, cesium, or francium.

As the above-described base, at least one kind selected from the metal hydroxides is preferable, and it is more preferable to use potassium hydroxide, sodium hydroxide, or potassium hydroxide and sodium hydroxide in combination.

A ratio of the base with respect to 234bb is preferably 0.2 to 2.5 mol, and more preferably 0.5 to 2.0 mol with respect to 1 mol of 234bb, from a viewpoint of improving the conversion ratio of 234bb and the selectivity of 1224yd.

The above-described base exists in the liquid phase in which the reaction (1) is carried out. The reaction (1) is preferably carried out in the liquid phase in the presence of the base and the solvent. The solvent is not particularly limited as long as it is a solvent capable of dissolving a predetermined amount of the above-described base and does not contribute to the above-described dehydrochlorination reaction. As the solvent to dissolve the above-described base, water is preferable because the solubility thereof with respect to the above-described base is high and water is inert with respect to the dehydrochlorination reaction. Specifically, in the reaction (1), the base is preferably used as an aqueous solution of the base. As the aqueous solution of the base, an aqueous solution of the alkali metal hydroxide is preferable, and an aqueous solution of sodium hydroxide or an aqueous solution of potassium hydroxide is more preferable.

A ratio of mass of the base with respect to the total mass of the solvent and the base is preferably an amount to be 10 to 50 mass %, and more preferably 20 to 40 mass %. When the amount of the base is equal to or more than the above-described lower limit value, a sufficient reaction rate is easily obtained, and it is easy to perform separation of the object through two-layer separation. When the amount of the base is equal to or less than the above-described upper limit value, the base is easily dissolved sufficiently and the metal salt is difficult to be precipitated, which is likely to be advantageous in an industrial process.

In the manufacturing method of the present invention, the solution obtained by dissolving the base in the solvent, 234bb, and other compounds taking part in the reaction and used according to need (denoted by a reference numeral 2) are supplied to the reactor 1 to carry out the reaction, as illustrated in FIG. 1. Although the generated composition containing 1224yd is recovered from the reactor 1, it is cooled via a cooler 3 according to need. In addition, it is preferable that the composition from which water is removed by being passed through a dehydration column 4 according to need, is recovered as a product 5.

As the reactor 1, a publicly-known reactor used for a dehydrochlorination reaction in a liquid phase reaction is preferable. As a material of the reactor 1, there can be cited iron, nickel, an alloy containing these as main components, glass, and so on. It is possible that lining processing such as resin lining or glass lining is performed on the reactor 1 according to need. Further, it is preferable that a stirring means is provided to the reactor 1, and the reaction is carried out while performing stirring, so that the reaction is carried out in a state where the raw material, the product, the base, the solvent, and the like are uniformly distributed in the reaction system.

A reaction temperature is a temperature in the reactor 1, and it is preferably 40 to 100° C., and more preferably 50 to 80° C. By making the reaction temperature fall within the aforementioned range, the reaction rate and the reaction ratio are improved, which enables to easily suppress by-products.

A pressure in the reactor during the reaction is preferably 0 to 10 MPa, more preferably 0.05 to 5 MPa, and still more preferably 0.15 to 1 MPa. The pressure in the reactor is preferably equal to or more than a vapor pressure of 234bb at the reaction temperature.

The reaction (1) can be performed in any of a semi-continuous mode, a batch mode, and a continuous mode. Note that a reaction time can be appropriately adjusted by a general method depending on each of the modes. The reaction time is preferably 1 to 50 hours in the batch mode, and it is preferably 1 to 3000 seconds in the continuous mode because it is easy to control the conversion ratio of 234bb being the raw material and the selectivity of 1224yd.

The reaction (1) may be performed in the presence of a phase-transfer catalyst in a range of exerting no influence on the reaction. It is possible to use a water-soluble organic solvent such as tetraglyme in a range of exerting no influence on the reaction. It is preferable to use the phase-transfer catalyst in order to increase the reaction rate.

As the phase-transfer catalyst, there can be cited a quaternary ammonium salt, a quaternary phosphonium salt, a quaternary arsonium salt, a sulfonium salt, crown ether, and so on, and among the above, the quaternary ammonium salt, the quaternary phosphonium salt, the quaternary arsonium salt, and the sulfonium salt are preferable, and the quaternary ammonium salt is more preferable.

As the quaternary ammonium salt, a compound represented by the following formula (i) can be cited.

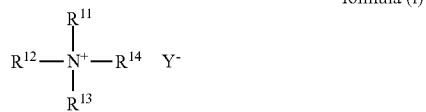

formula (i)

Note that in the formula (i), $R^{11}$ to $R^{14}$ each independently represent a monovalent hydrocarbon group, or a monovalent hydrocarbon group to which a functional group inert to a reaction is bonded, and $Y^-$ represents an anion.

When $R^{11}$ to $R^{14}$ are each the hydrocarbon group, there can be cited an alkyl group, a cycloalkyl group, an alkenyl group, a cycloalkenyl group, an aryl group, or the like, and the alkyl group or the aryl group is preferable. The number of carbon atoms of $R^{11}$ to $R^{14}$ is preferably 4 to 100, and more preferably 6 to 30. $R^{11}$ to $R^{14}$ may be each the same group or may be groups different from one another.

A functional group when $R^{11}$ to $R^{14}$ are each the monovalent hydrocarbon group to which a functional group inert to a reaction is bonded is appropriately selected depending on reaction conditions, and there can be cited a halogen atom, an alkoxycarbonyl group, an acyloxy group, a nitrile group, an acyl group, a carboxyl group, an alkoxyl group, or the like.

As quaternary ammonium ($R^{11}R^{12}R^{13}R^{14}N^+$) in the formula (i), there can be cited tetramethylammonium, tetraethylammonium, tetra-n-propylammonium, tetra-n-butylammonium, methyltri-n-octylammonium, cetyltrimethylammonium, benzyltrimethylammonium, benzyltriethylammonium, cetylbenzyldimethylammonium, cetylpyridinium, n-dodecylpyridinium, phenyltrimethylammonium, phenyltriethylammonium, N-benzylpicolinium, pentamethonium, hexamethonium, or the like.

As $Y^-$ in the formula (i), there can be cited a fluorine ion, a chlorine ion, a bromide ion, an iodine ion, a sulfate ion, a nitrate ion, a phosphate ion, a perchlorate ion, a hydrogen sulfate ion, a hydroxide ion, an acetate ion, a benzoate ion, a benzenesulfonate ion, a p-toluenesulfonate ion, or the like, and among the above, the fluorine ion, the chlorine ion, the bromide ion, the iodine ion, the hydrogen sulfate ion, or the hydroxide ion is preferable, the fluorine ion, the chlorine ion, the bromide ion, the iodine ion, the hydroxide ion is more preferable, and the chlorine ion or the bromide ion is still more preferable.

As the compound represented by the formula (i), combinations of the following quaternary ammonium ($R^{11}R^{12}R^{13}R^{14}N^+$) and the following $Y^-$ are preferable from a viewpoint of general versatility and reactivity.

Quaternary ammonium ($R^{11}R^{12}R^{13}R^{14}N^+$): tetramethylammonium, tetraethylammonium, tetra-n-propylammonium, tetra-n-butylammonium, or methyltri-n-octylammonium. $Y^-$: a fluorine ion, a chlorine ion, a bromide ion, an iodine ion, or a hydroxide ion.

The quaternary ammonium salt is preferably at least one selected from a group consisting of tetra-n-butylammonium chloride (TBAC), tetra-n-butylammonium bromide (TBAB), and methyltri-n-octylammonium chloride (TOMAC).

As the quaternary phosphonium salt, a compound represented by the following formula (ii) can be cited.

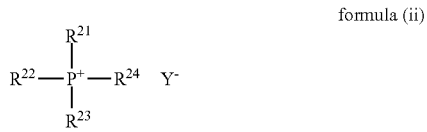

formula (ii)

Note that in the formula (ii), $R^{21}$ to $R^{24}$ each independently represent a monovalent hydrocarbon group, and $Y^-$ represents an anion. $R^{21}$ to $R^{24}$ may be each the same group or may be groups different from one another.

As the hydrocarbon group in each of $R^{21}$ to $R^{24}$, there can be cited an alkyl group, a cycloalkyl group, an alkenyl group, a cycloalkenyl group, an aryl group, or the like, and the alkyl group or the aryl group is preferable.

As quaternary phosphonium ($R^{21}R^{22}R^{23}R^{24}P^+$) in the formula (ii), there can be cited tetraethylphosphonium, tetra-n-butylphosphonium, ethyltri-n-octylphosphonium, cetyltriethylphosphonium, cetyltri-n-butylphosphonium, n-butyltriphenylphosphonium, n-amyltriphenylphosphonium, methyltriphenylphosphonium, benzyltriphenylphosphonium, tetraphenylphosphonium, or the like.

As $Y^-$, there can be cited a chlorine ion, a fluorine ion, a bromide ion, an iodine ion, a sulfate ion, a nitrate ion, a phosphate ion, a perchlorate ion, a hydrogen sulfate ion, a hydroxide ion, an acetate ion, a benzoate ion, a benzenesulfonate ion, a p-toluenesulfonate ion, or the like, and the fluorine ion, the chlorine ion, or the bromide ion is preferable.

As the quaternary arsonium salt, a compound represented by the following formula (iii) can be cited.

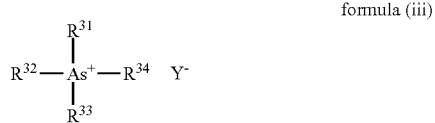

formula (iii)

Note that in the formula (iii), $R^{31}$ to $R^{34}$ are the same as $R^{21}$ to $R^{24}$ in the formula (ii), and preferable modes thereof are also the same. $Y^-$ represents an anion. As $Y^-$, a halogen ion is preferable, and a fluorine ion, a chlorine ion, or a bromide ion is more preferable.

As the quaternary arsonium salt represented by the formula (iii), there can be cited triphenylmethylarsonium fluoride, tetraphenylarsonium fluoride, triphenylmethylarsonium chloride, tetraphenylarsonium chloride, tetraphenylarsonium bromide, or the like. As the quaternary arsonium salt, triphenylmethylarsonium chloride is preferable.

As the sulfonium salt, a compound represented by the following formula (iv) can be cited.

formula (iv)

Note that in the formula (iv), $R^{41}$ to $R^{43}$ and $Y^-$ are the same as $R^{31}$ to $R^{34}$ and $Y^-$ in the formula (iii), and preferable modes thereof are also the same.

As the sulfonium salt represented by the formula (iv), there can be cited di-n-butylmethylsulfonium iodide, tri-n-butylsulfonium tetrafluoroborate, dihexylmethylsulfonium iodide, dicyclohexylmethylsulfonium iodide, dodecylmethylethylsulfonium chloride, tris(diethylamino)sulfonium difluorotrimethylsilicate, or the like. As the sulfonium salt, dodecylmethylethylsulfonium chloride is preferable.

As the crown ether, there can be cited 18-crown-6, dibenzo-18-crown-6, dicyclohexyl-18-crown-6, or the like.

The use amount of the phase-transfer catalyst is preferably 0.01 to 10 parts by mass, more preferably 0.05 to 5.0 parts by mass, and still more preferably 0.1 to 1.0 part by mass with respect to 100 parts by mass of 234bb. When the amount of the phase-transfer catalyst falls within the aforementioned range, a sufficient reaction rate is easily obtained. When the amount of the phase-transfer catalyst is out of the aforementioned range, a reaction accelerating effect is difficult to be obtained, which is likely to be disadvantageous in terms of cost. When the phase-transfer catalyst is used, it is preferable that the phase-transfer catalyst is previously mixed in 234bb, and it is supplied to the reactor in a state of mixed solution with 234bb.

The reaction step, the reaction device, and the material of the reactor when the phase-transfer catalyst is used, may be the same as those when the phase-transfer catalyst is not used. Further, the reaction conditions such as the concentration of the base, the use amount, and the reaction temperature may be the same as those when the phase-transfer catalyst is not used.

The reaction (1) can be progressed in a manner that, for example, 234bb, the base, the solvent according to need, and the compound which takes part in the reaction such as the phase-transfer catalyst according to need, are supplied to the reactor, stirring is performed to uniformize these, and desired temperature condition and pressure condition are provided.

When, for example, the aqueous solution of alkali metal hydroxide or the like is used as the solution obtained by dissolving the base in the solvent, the reaction system is separated into an aqueous phase and an organic phase. In such a case, by using, for example, a water-soluble organic solvent such as tetraglyme in place of the phase-transfer catalyst to compatibilize the aqueous phase containing the base and the organic phase, the reaction (1) can be carried out. When the water-soluble organic solvent is used, it is preferable to sufficiently perform stirring to create a uniform state of the compounds that take part in the reaction in the reaction system.

When a reaction solution after the completion of the reaction is left as it is to be separated into an organic phase and an aqueous phase, the organic phase may contain a by-product other than unreacted 234bb and 1224yd being the object product. As the by-product, there can be cited 1-chloro-3,3,3-trifluoropropyne which is produced when 1224yd is further subjected to dehydrochlorination. Further, when 234bb containing impurities is used as the raw material, there is a case where 1,1-dichloro-2,3,3,3-tetrafluoropropene (CFO-1214ya) or the like is contained as the by-product.

The product obtained by the reaction (1) contains unreacted 234bb, the above-described by-product, and the like, other than 1224yd being the object product. The substances other than 1224yd being the object product can be easily removed through a method in which they are distilled to be separated, or the like.

According to the manufacturing method of the present invention, it is possible to manufacture 1224yd which is useful as a working fluid for a heat cycle system having a small global warming potential, from 234bb, with a high conversion ratio and high selectivity, through an economically advantageous method which can be industrially carried out.

EXAMPLES

Hereinafter, the present invention will be concretely described by using working examples, but, the present invention is not limited to these working examples. Manufacturing examples 1 to 6 are manufacturing examples of 234bb. Further, examples 1 to 4 are working examples in the manufacture of 1224yd.

[Analysis Condition]

In the following manufacturing examples and examples, a chemical composition analysis of an obtained product was performed by using gas chromatography (GC). DB-1301 (product name, manufactured by Agilent Technologies, Inc., 60 m in length×250 μm in inside diameter×1 μm in thickness) was used as a column. Analysis results of the obtained products are shown in Table 1 or Table 2.

Manufacturing Example 1

1234yf obtained by a publicly-known method was chlorinated to manufacture 234bb. First, a reactor made of stainless steel (with internal volume of 2.3 L) to which a quartz pipe and a jacket that transmit light from a light source were attached, was cooled to 0° C. In this reactor, 1395 g of carbon tetrachloride ($CCl_4$) was put as a solvent, and thereafter, while irradiating visible light from a fluorescent light (manufactured by TOSHIBA CORPORATION, product name: Neo Compact, bulb-type: EFP12EL, output of 12 W), 1234yf was supplied into the reactor at a flow rate of 245 g per hour, and chlorine gas was supplied into the reactor at a flow rate of 152 g per hour. In accordance with the progress of the reaction, a heat of reaction was generated, and a temperature in the reactor was raised to 7.6° C. and a pressure in the reactor was raised to 0.08 MPa. The reaction was continuously carried out for one hour while supplying 1234yf and the chlorine gas at the aforementioned flow rates, respectively, and after confirming that 245 g of 1234yf and 152 g of the chlorine gas were supplied, the supply of 1234yf and the chlorine gas was stopped, and the light irradiation was continued until the pressure in the reactor became an atmospheric pressure.

After the completion of the reaction, the obtained reaction solution was neutralized by 20 mass % of potassium bicarbonate aqueous solution, and then liquid separation operation was performed. After still standing, a product (1) of 1734 g was recovered from a separated lower layer. The product (1) was distilled through an ordinary operation, to thereby obtain 234bb with a purity of 99.8%.

Manufacturing Example 2

To the reactor used in the manufacturing example 1, an electromagnetic valve capable of being automatically opened or closed by a timer was connected. 234bb (with a purity of 99.8%) obtained in the manufacturing example 1 of 1800 g was used as a solvent.

While irradiating visible light with the fluorescent light in the manufacturing example 1, 1234yf and the chlorine gas were supplied similarly to the manufacturing example 1. 1234yf was adjusted in stages for ten several minutes from a time several minutes after the start of the supply thereof so that its flow rate became 1070 g per hour, and after the flow rate became 1070 g per hour, the supply thereof was continued at this flow rate. The chlorine gas was also adjusted in stages similarly to 1234yf so that its flow rate became 666 g per hour, and after the flow rate became 666 g per hour, the supply thereof was continued at this flow rate. The reaction was carried out for 8 hours while continuously extracting the product to make an amount of solution in the reactor to be constant. The total supply amount of 1234yf was 8327 g, and the total supply amount of the chlorine gas was 5028 g. Further, a temperature in the reactor was 36 to 39° C., and a pressure in the reactor was 0.18 MPa.

The product extracted from the reactor was neutralized similarly to the manufacturing example 1, thereby recovering a product (2) of 15048 g.

Manufacturing Example 3

As the solvent, 1917 g of the product (2) obtained in the manufacturing example 2 was used. 1234yf and the chlorine gas whose flow rates were adjusted through a method similar to that of the manufacturing example 2 were supplied into the reactor for 8.5 hours. A supply rate of 1234yf at this time was 1221 g per hour, and a supply rate of the chlorine gas was 760 g per hour. The total supply amount of 1234yf was 9991 g, and the total supply amount of the chlorine gas was 6154 g. A temperature in the reactor was 49 to 51° C., and a pressure in the reactor was 0.24 MPa. Similarly to the manufacturing example 2, 17884 g of a product (3) was obtained.

Manufacturing Example 4

As the solvent, 2468 g of the product (3) obtained in the manufacturing example 3 was used. 1234yf and the chlorine gas whose flow rates were adjusted through a method similar to that of the manufacturing example 2 were supplied into the reactor for 6 hours. A supply rate of 1234yf at this time was 1068 g per hour, and a supply rate of the chlorine gas was 660 g per hour. Operations similar to those of the manufacturing example 2 were performed except that the supply amounts of 1234yf and the chlorine gas were set as described above. The total supply amount of 1234yf was 6669 g, and the total supply amount of the chlorine gas was 4209 g. A temperature in the reactor was 53 to 57° C., and a pressure in the reactor was 0.24 MPa. Operations similar to those of the manufacturing example 2 were performed, to thereby obtain 13098 g of a product (4).

Manufacturing Example 5

An internal volume of the reactor was set to 4.5 L, a light source to be used was set to an LED lamp (manufactured by Mitsubishi Electric Corporation, bulb-type: LHT15D-G-E39, output of 15 W), and as the solvent, 3000 g of the product (4) obtained in the manufacturing example 4 was used. 1234yf and the chlorine gas whose flow rates were adjusted through a method similar to that of the manufacturing example 2 were supplied into the reactor for 6 hours. A supply rate of 1234yf at this time was 1069 g per hour, and a supply rate of the chlorine gas was 666 g per hour. Operations similar to those of the manufacturing example 2 were performed except that the supply rates of 1234yf and the chlorine gas were set as described above. The total supply amount of 1234yf was 6420 g, and the total supply amount of the chlorine gas was 3990 g. A temperature in the reactor was 14 to 15° C., and a pressure in the reactor was 0.06 MPa. Operations similar to those of the manufacturing example 2 were performed, to thereby obtain 10110 g of a product (5).

Manufacturing Example 6

In the reactor same as that used in the manufacturing example 1, 1323 g of $CCl_4$ was put, and thereafter, while irradiating ultraviolet light having a characteristic line spectrum in a wavelength of 250 to 320 nm and a wavelength of 360 nm from a high-pressure mercury lamp (manufactured by Eikosha, output of 400 W), 1234yf was supplied into the reactor at a flow rate of 245 g per hour, and the chlorine gas was supplied into the reactor at a flow rate of 152 g per hour. In accordance with the progress of the reaction, a heat of reaction was generated, and a temperature in the reactor was raised to 9.8° C. and a pressure in the reactor was raised to 0.14 MPa. The reaction was continuously carried out for one hour while supplying 1234yf and the chlorine gas at the aforementioned flow rates, respectively, and after confirming that the total supply amount of 1234yf became 245 g, and the total supply amount of the chlorine gas became 152 g, the supply of 1234yf and the chlorine gas was stopped, and the ultraviolet light irradiation was continued until the pressure in the reactor became an atmospheric pressure.

After the completion of the reaction, 1412 g of a product (6) was obtained through operations similar to those of the manufacturing example 1.

GC analysis results of the products (1) to (6) obtained in the manufacturing examples 1 to 6 are shown in Table 1. In Table 1, a conversion ratio of 1234yf indicates a ratio (unit:mol %) of an amount of 1234yf consumed due to the reaction with respect to the total amount of 1234yf supplied to the reactor. Further, selectivity of each compound indicates a ratio (unit:mol %) of each compound with respect to the total amount of the entire product.

Note that the conversion ratio of 1234yf and the selectivity of each compound in each of the manufacturing examples 2 to 5 whose reaction mode was the continuous mode, were calculated from the GC analysis results of an extracted solution obtained after 5 hours or more from the start of the reaction. Further, in each of the manufacturing examples 2 to 5, regarding the selectivity of 234bb, an amount as a result of removing 234bb initially supplied as the solvent from 234bb in the product, was determined as a production amount (mol) of 234bb.

TABLE 1

|  |  | Manufacturing example 1 | Manufacturing example 2 | Manufacturing example 3 | Manufacturing example 4 | Manufacturing example 5 | Manufacturing example 6 |
|---|---|---|---|---|---|---|---|
| Reaction mode | | Batch mode | Continuous mode | Continuous mode | Continuous mode | Continuous mode | Batch mode |
| Irradiation light source | | Fluorescent light | Fluorescent light | Fluorescent light | Fluorescent light | LED | High-pressure mercury lamp |
| Product composition [mol %] | 1234yf | 0.28 | 0.64 | 0.29 | 0.22 | 0.45 | 0.012 |
| | 234bb | 19.34 | 97.33 | 95.45 | 94.05 | 97.90 | 11.20 |
| | 224ba | 0.012 | 1.41 | 3.87 | 5.33 | 0.88 | 5.88 |
| | 214ba | 0.10 | 0.12 | 0.26 | 0.32 | 0.01 | 1.78 |
| | $CCl_4$ | 80.14 | 0.041 | 0.010 | 0.00 | 0.00 | 80.04 |
| | Others | 0.13 | 0.46 | 0.12 | 0.08 | 0.75 | 1.09 |
| Reaction result [mol %] | 1234yf conversion ratio | 98.6 | 99.4 | 99.7 | 99.8 | 99.6 | 99.9 |
| | Selectivity 234bb | 98.8 | 98.0 | 95.7 | 94.3 | 98.3 | 57.2 |
| | 224ba | 0.1 | 1.4 | 3.9 | 5.3 | 0.9 | 30.0 |
| | 214ba | 0.5 | 0.1 | 0.3 | 0.3 | 0.0 | 9.1 |
| | Others | 0.6 | 0.5 | 0.1 | 0.1 | 0.8 | 3.7 |

As can be seen from Table 1, according to the manufacturing examples 1 to 5 each using the light source capable of efficiently irradiating the light with the wavelength of 400 to 750 nm, it is possible to suppress the generation of by-products to obtain 234bb being the object with high selectivity, when compared to the manufacturing example 6 in which the ultraviolet light with the wavelength of less than 400 nm was irradiated.

Example 1

A tube reactor made of a fluorine-based resin with an outside diameter of ½ inch and a length of 30 m (with internal volume of 1 L) in which a resin static mixer manufactured by NORITAKE CO., LIMITED was installed, was used as the reactor. The reactor was installed in a constant temperature bath, and a reaction temperature was set to 60° C. The KOH aqueous solution of 20 mass % was supplied to the reactor at a flow rate of 4550 g per hour, and a 234bb mixed solution in which tetra-n-butylammonium bromide (TBAB) was mixed to be 1 mass % was supplied to the reactor at a flow rate of 1500 g per hour. Next, a pressure in the reactor was regulated to be 0.2 MPa by a pressure-regulating valve installed at an outlet of the reactor, and the reaction was continuously carried out for 8 hours. 234bb used in the example 1 is 234bb (with a purity of 99.8%) obtained through the distillation in the manufacturing example 1.

The product obtained in the reactor was extracted into a tank with jacket at an atmospheric pressure and whose temperature was kept at 60° C. The extracted product was turned into gas to be taken out from a gas phase part, and recovered in the tank with jacket cooled to −20° C. The recovered product was turned into gas at 60° C. to be sampled, and then the GC analysis was carried out.

Example 2

The reaction was caused similarly to the example 1, except that the temperature in the reactor was changed from 60° C. to 70° C. The product obtained in the reactor was recovered through an operation similar to that of the example 1, and then the GC analysis was carried out.

Example 3

The reaction was caused similarly to the example 1, except that the temperature in the reactor was set to 70° C., the supply rate of 20 mass % of KOH aqueous solution to the reactor was set to 6304 g per hour, and the supply rate of 234bb in which TBAB was mixed to be 1 mass % to the reactor was set to 2160 g per hour. The obtained product was recovered through an operation similar to that of the example 1, and then the GC analysis was carried out.

The reaction conditions and the GC analysis results of the obtained products in the examples 1 to 3 are shown in Table 2. In Table, the conversion ratio of 234bb indicates a ratio (mol %) of an amount of 234bb consumed due to the reaction with respect to the total amount of 234bb supplied to the reactor. Further, the selectivity of each compound indicates a ratio (mol %) of generated each component with respect to converted 234bb, and is calculated from the GC analysis result of gas vaporized at 40° C.

TABLE 2

|  |  |  | Example 1 | Example 2 | Example 3 |
|---|---|---|---|---|---|
| Reaction mode | | | Continuous mode | Continuous mode | Continuous mode |
| Reaction condition | KOH/234bb(molar ratio) | | 2.00 | 2.00 | 1.92 |
| Product composition [mol %] | 1224yd(Z) | | 88.94 | 88.12 | 88.87 |
| | 1224yd(E) | | 5.17 | 5.76 | 6.07 |
| | 234bb | | 4.24 | 1.47 | 2.97 |
| | Others | | 1.64 | 4.65 | 2.09 |
| | Total | | 100 | 100 | 100 |
| Reaction result [mol %] | 234bb conversion ratio | | 95.8 | 98.5 | 97.0 |
| | Selectivity | 1224yd(Z) | 92.9 | 89.4 | 91.6 |
| | | 1224yd(E) | 5.4 | 5.8 | 6.3 |
| | | Others | 1.7 | 4.8 | 2.1 |

Example 4

The product (3) obtained in the manufacturing example 3 was used in place of 234bb in the example 1, and the reaction was caused similarly to the example 1. The obtained product was recovered similarly to the example 1, and the GC analysis was carried out.

The reaction conditions and the GC analysis results of the obtained product in the example 4 are shown in Table 3. In Table 3, the selectivity of 1224yd as a product derived from 234bb was calculated, and the selectivity of 1214ya as a product derived from 224ba was calculated.

TABLE 3

|  |  | Example 4 |
|---|---|---|
| Reaction mode |  | Continuous mode |
| Use amount [mol] | 234bb in unrefined 234bb | 62 |
| Reaction condition | KOH/234bb(molar ratio) | 2.08 |
| Product composition [mol %] | 1234yf | 0.21 |
|  | 1224yd(E) | 5.91 |
|  | 1224yd(Z) | 86.37 |
|  | 1214ya | 3.25 |
|  | 234bb | 3.78 |
|  | 224ba | 0.01 |
|  | 214bb | 0.15 |
|  | Others | 0.31 |
|  | Total | 100 |
| Reaction result [mol %] | 234bb conversion ratio | 96.1 |
|  | Selectivity 1224yd(Z) | 93.4 |
|  | 1224yd(E) | 6.4 |
|  | Others | 0.2 |
|  | 224ba conversion ratio | 99.7 |
|  | Selectivity 1214ya | 99.6 |
|  | Others | 0.4 |

As can be seen from Table 2, 3, according to the examples 1 to 4, it is possible to manufacture 1224yd being an object with high selectivity and high yield by suppressing generation of by-products. Further, since the selectivity of 1224yd (Z) having higher chemical stability and which is more useful as a working fluid for a heat cycle system when compared to 1224yd (E) is high, the manufacturing method of 1224yd of the present invention is industrially advantageous as a manufacturing method of a working fluid for a heat cycle system.

What is claimed is:

1. A manufacturing method of 1-chloro-2,3,3,3-tetrafluoropropene, comprising;
   subjecting 1,2-dichloro-2,3,3,3-tetrafluoropropane to a dehydrochlorination reaction at a reaction temperature of 50 to 100° C. in a liquid phase in the presence of a base.
2. The manufacturing method according to claim 1, wherein
   1,2-dichloro-2,3,3,3-tetrafluoropropane is subjected to the dehydrochlorination reaction in the liquid phase in the presence of a solvent to dissolve the base, and the base.
3. The manufacturing method according to claim 1, wherein
   the base is selected from a group consisting of a metal hydroxide, a metal oxide, and a metal carbonate, or a mixture thereof.
4. The manufacturing method according to claim 1, wherein
   the base is used in a ratio of 0.2 to 2.5 mol with respect to 1 mol of the 1,2-dichloro-2,3,3,3-tetrafluoropropane.
5. The manufacturing method according to claim 1, wherein
   a reaction temperature in the dehydrochlorination reaction is 60 to 100° C.
6. The manufacturing method according to claim 2, wherein
   the solvent is water.
7. The manufacturing method according to claim 2, wherein
   an amount of the base is 10 to 50 mass % with respect to total mass of the solvent and the base.
8. The manufacturing method according to claim 1, wherein
   the dehydrochlorination reaction is performed in a presence of a phase-transfer catalyst.
9. The manufacturing method according to claim 8, wherein
   the phase-transfer catalyst is a quaternary ammonium salt.
10. The manufacturing method according to claim 9, wherein
    the quaternary ammonium salt is selected from a group consisting of tetra-n-butylammonium chloride, tetra-n-butylammonium bromide, and methyltri-n-octylammonium chloride, or a mixture thereof.
11. The manufacturing method according to claim 1, further comprising;
    reacting 2,3,3,3-tetrafluoropropene with chlorine to produce 1,2-dichloro-2,3,3,3-tetrafluoropropane.
12. The manufacturing method according to claim 11, wherein
    a reaction of the 2,3,3,3-tetrafluoropropene and chlorine is caused under irradiation of light in a wavelength region of 400 to 750 nm.

* * * * *